United States Patent [19]

Ligtvoet et al.

[11] Patent Number: 4,904,683

[45] Date of Patent: Feb. 27, 1990

[54] EMULSIFIABLE CONCENTRATES CONTAINING AZOLES

[75] Inventors: Theo F. M. C. Ligtvoet, Vlimmeren; Paul F. M. Ruelens, Herk-de-Stad, both of Belgium

[73] Assignee: Janssen Pharmaceutica N.V., Beerse, Belgium

[21] Appl. No.: 242,653

[22] Filed: Sep. 12, 1988

Related U.S. Application Data

[63] Continuation of Ser. No. 59,209, Jun. 3, 1987, abandoned, which is a continuation of Ser. No. 689,266, Jan. 7, 1985, abandoned, which is a continuation-in-part of Ser. No. 587,096, Mar. 7, 1984, abandoned.

[51] Int. Cl.$^4$ .......................................... A61K 31/415
[52] U.S. Cl. ..................................... 514/397; 514/383; 514/396; 514/399
[58] Field of Search ...................... 514/399, 396, 397

[56] References Cited

U.S. PATENT DOCUMENTS

| 4,237,158 | 12/1980 | Miller | 514/399 |
| 4,368,186 | 1/1983 | Vickery | 514/399 |
| 4,423,057 | 12/1983 | Walker | 514/399 |
| 4,446,145 | 5/1984 | Van Bever | 514/399 |

Primary Examiner—C. Warren Ivy
Attorney, Agent, or Firm—Charles J. Metz

[57] ABSTRACT

Formulations being compatible with aqueous and non-aqueous mediums, said formulations containing an azole, a solvent and an emulsifying agent.

11 Claims, No Drawings

EMULSIFIABLE CONCENTRATES CONTAINING AZOLES

CROSS-REFERENCE TO RELATED APPLICATION

This is a continuation of application Ser. No. 59,209, filed June 3, 1987, now abandoned, which is in turn a continuation of application Ser. No. 689,266, filed Jan. 7, 1985, now abandoned, which is a continuation-in-part of our co-pending application Ser. No. 587,096 filed Mar. 7, 1984, now abandoned.

DESCRIPTION OF THE INVENTION

1H-Imidazoles and 1H-1,2,4-triazoles having attractive antimicrobial properties have been described in, for example, U.S. Pat. Nos. 3,575,999; 3,717,655; 3,658,813; 3,927,017; 4,156,008; and 4,079,062, and in British Patent Nos. 2,026,486; 2,027,701 and 1,589,852.

Due to their antimicrobial properties the hereinabove-mentioned azoles are very useful in the protection of living subjects and non-living organic materials against decay caused by microorganisms. Living subjects are meant to include human and animal beings as well as plants. Non-living organic materials are meant to include any material which has a substantially organic nature such as, for example, wood, coatings, harvested fruits, foodstuffs, medicines and the like.

The above-mentioned azoles are usually handled in the form of a suitable formulation which may be applied as such or after diluting with a suitable medium. Depending upon the nature of the azole incorporated and the nature of the subjects or materials where the formulation is applied to the said formulations may have a predominantly aqueous or organic nature.

Furthermore, in order to have sufficient protection it may be desirable to combine an azole with an additional active ingredient such as, for example, a pesticide, e.g., an additional fungicide, insecticide and the like. Said additional active ingredient may be incorporated in the initial formulation or the ultimate mixture may be prepared by adding at least two formulations to an appropriate medium, e.g. an aqueous or an organic medium.

Since each active compound is preferably formulated in a medium appropriate for said compound it is not unusual that by combining two or more active ingredients the resulting formulation does not meet the requirements of stability and the like properties which are necessary or, at least, desirable for handling and/or applying the initial-, respectively the resulting formulation.

The present invention is concerned with azole containing formulations which are highly compatible with any aqueous or non-aqueous medium, said azoles being selected from the group consisting of 1H-imidazoles and 1-H-1,2,4-triazoles having the formula

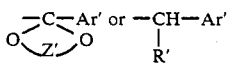

or an acid addition salt thereof, wherein X is —N= or —CH= and $R_1$ is a radical of the formula

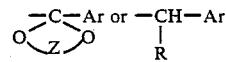

wherein Z is a group —CH$_2$—CH$_2$—, —CH$_2$—CH$_2$—CH$_2$—, —CH(CH$_3$)—CH(CH$_3$)— or —CH$_2$—CH(alkyl)—, wherein said alkyl is a straight or branched $C_1$-$C_{10}$ alkyl radical; said Ar is a phenyl group which is optionally substituted with 1 to 3 halogens, $C_1$-$C_6$ alkyl radicals, $C_1$-$C_6$ alkoxy radicals, cyano-, trifluoromethyl- or nitro groups, a thienyl-, halothienyl-, naphthalenyl- or fluorenyl group; and, said R is $C_1$-$C_{10}$ alkyl, cycloalkyl, cycloalkyllower alkyl, lower alkenyl, aryllower alkyl, aryloxylower alkyl or a radical of the formula —O—$R_o$, wherein said $R_o$ is $C_1$-$C_{10}$ alkyl, lower alkenyl, lower alkynyl or aryllower alkyl, wherein said aryl radical is phenyl, naphthalenyl or substituted phenyl, wherein said substituted phenyl has 1 to 3 substituents selected from the group consisting of halo, cyano, nitro, phenyl, lower alkyl and lower alkoxy, provided that when more than one substituent is present only one thereof may be cyano, nitro or phenyl.

The subject formulations compatible with any aqueous or non-aqueous medium contain:
  (i) from 1% to 60% w/v of an azole of formula (I);
  (ii) from 1% to 60% w/v of an emulsifying agent; and
  (iii) from 1% to 98% w/v of a solvent.

Particularly interesting formulations contain an azole of formula

or an acid addition salt thereof, wherein X has the above-identified meaning and $R_1'$ is a radical of the formula

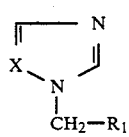

wherein Z' is a group —CH$_2$—CH$_2$—, —CH$_2$—CH$_2$—CH$_2$—, —CH(CH$_3$)—CH$_2$—, —CH(C$_2$H$_5$)—CH$_2$—, —CH(C$_3$H$_7$)—CH$_2$—, —CH(CH$_3$)—CH(CH$_3$)— or —CH(CH$_3$)—CH(C$_2$H$_5$)—; Ar' is unsubstituted phenyl or phenyl substituted with 1 to 3 halogen atoms, preferably chloro atoms, $C_1$-$C_6$ alkyl radicals, $C_1$-$C_6$ alkoxy radicals, cyano or nitro groups; and R' is $C_1$-$C_6$ alkyl or $C_3$-$C_4$ alkenyloxy.

More particularly interesting formulations contain an azole of formula

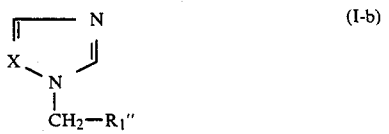

or an acid addition salt thereof, wherein X has the above-identified meaning and $R_1''$ is a radical of the formula

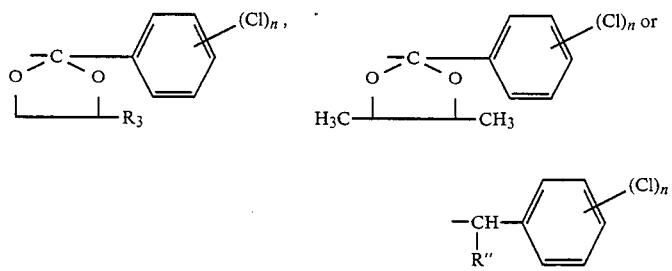

wherein R" is $C_1$–$C_4$ alkyl or $C_3$–$C_4$ lower alkenyloxy, $R_3$ is hydrogen or $C_1$–$C_3$ alkyl and n is 1 or 2.

Preferred formulations in accordance with the present invention are those containing 1-[2-(2,4-dichlorophenyl)-2-(2-propenyloxy)ethyl]-1H-imidazole, generically designated as imazalil, or a suitable acid addition salt thereof.

The solvent of the formulation is intended to fulfil the requirements of sufficiently solubilizing the azole and, if desired, any additional active ingredient. Furthermore, the solvent must be homogeneously miscible with the emulsifying agent used in the formulation.

Due to their desirable solubilizing effect and their compatibility with a wide range of emulsifying agents alkanedioles such as, for example, 1,2-ethanediol, 1,2-propanediol and 1,3-propanediol, are particularly preferred. Even more particularly preferred is 1,2-propanediol since this solvent combines an excellent solubilizing effect with a desirably high flash-point.

Since the subject formulations must be compatible with a wide range of mediums and/or additives the said formulations must contain a suitable amount of a non-ionic emulsifying agent.

Due to their desirable solubilizing effect, their good solubility in a wide range of aqueous and non-aqueous mediums and their compatibility with the said mediums and a wide range of possible additives, e.g. co-emulsifying agents and additional active ingredients, the emulsifying agent is preferably selected from the group consisting of:

(i) addition products of 1 to 60 moles of ethylene oxide with 1 mole of a phenol which is further substituted with at least one $C_1$–$C_{15}$ alkyl group;

(ii) addition products of 1 to 60 moles of ethylene oxide with 1 mole of ricinus oil;

(iii) addition products of 1 to 60 moles of ethylene oxide with 1 mole of a lanoline derivative;

(iv) addition products of 1 to 60 moles of ethylene oxide or propylene oxide with 1 mole of a fatty alcohol; and (v) cobloc polymers consisting of polyethylene oxide and polypropylene oxide blocs.

Because of their highly attractive properties cobloc polymers of polyethylene oxide and polypropylene oxide are particularly preferred.

Where the selection of the cobloc polymer is less critical as concerns the compatibility of the subject formulations with an organic medium it has been found that the said selection is more critical as concerns the compatibility of the subject formulations with an aqueous medium. Therefore, the more preferred emulsifying agent is a cobloc polymer containing from 30% to 60% of ethylene oxide and having a molar mass of the polypropylene oxide block of 950 to 5000 g per mole.

The most preferred cobloc polymer contains 50% of polyethylene oxide and has a molar mass of 3250 polypropylene oxide block per mole.

In addition to the azole, a possible additional active ingredient, a solvent and an emulsifying agent the formulations may also contain one or more additives. Such additives may be added to the formulations in order to ameliorate the properties of the initial formulations or of the formulations finally applied.

A suitable additives is, for example, a co-emulsifying agent which effects that by mixing the initial formulation with an aqueous or organic medium the resulting dilution is much more stable. Suitable co-emulsifying agents are, for example, ($C_6$–$C_{34}$)alkyl benzenesulfonic acid.

In the formulations of the present invention the azoles can also be used in combination with other compounds having a useful activity such as, biocidal compounds, e.g. antimicrobial agents, insecticides and the like.

As antimicrobial agents, which may be used in combination with the azoles there may be considered products of the following classes:

Phenol derivatives such as 3,5-dichlorophenol, 2,5-dichlorophenol, 3,5-dibromophenol, 2,5-dibromophenol, 2,5-(resp. 3,5)-dichloro-4-bromophenol, 3,4,5-trichlorophenol; chlorinated hydrodiphenylethers such as, for example, 2-hydroxy-3,2'4'-trichlorodiphenylether, phenylphenol, 4-chloro-2-phenylphenol, 4-chloro-2-benzylphenol, dichlorophene, hexachlorophene; aldehydes such as formaldehyde, glutaraldehyde, salicylaldehyde; alcohols such as phenoxyethanol; antimicrobially active carboxylic acids and their derivatives; organometallic compounds such as tributyltin compounds; iodine compounds such as iodophores, iodonium compounds; mono-, di and polyamines such as dodecylamine or 1,10-di(n-heptyl)-1,10-diaminodecane; quaternary ammonium compounds such as benzyl-dimethyldodecylammonium chloride, dimethyldodecylammonium chloride, benzyldi(2-hydroxyethyl)dodecylammonium chloride; sulfonium and phosphonium compounds; mercapto compounds as well as their alkali, earth alkaline and heavy metal salts such as 2-mercaptopyridine-N-oxide and its sodium and zinc salt, 3-mercaptopyridazin-2-oxide, 2-mercaptoquinoxaline-1-oxide, 2-mercaptoquinoxaline-di-N-oxide, as well as the symmetrical disulfides of said mercapto compounds; ureas such as tribromo or trichlorocarbanilide, dichlorotrifluoromethyldiphenylurea; tribromosalicylanilide; 2-bromo-2-nitro-1,3-dihydroxypropane; dichlorobenzoxazolon; chlorohexidine; isothia- and benzisothiazolone derivatives.

As insecticidal agents which may be used in combination with the azoles the following classes of products may be considered: insecticides having a natural origin, e.g., nicotine, rotenone, pyrethrum and the like; chloridinated hydrocarbons, e.g., lindane, chlordane, endosulfan and the like; organic phosphor compounds; carbamates, e.g., carbaryl, aldicarb, methiocarb, propoxur and the like; biological insecticides, e.g., products originating from *Bacillus thuringiensis;* synthetic pyrethroids, e.g. permethrin, allethrin, cypermethrin, halothrin and the like.

Besides their high compatibility with aqueous and non-aqueous mediums the subject formulations are particularly attractive for incorporating relatively high doses of azoles and, if desired, other active ingredients.

Preferred concentrated formulations contain from 20% to 60% w/v of an azole.

By combining a high compatibility for aqueous and non-aqueous mediums with a capacity for incorporating relatively high doses of azoles and, if desired, other active ingredients the subject formulations are particularly attractive for handling concentrated azole containing mixtures which are usually applied to subjects or materials in relatively diluted mixtures. Diluted mixtures are meant to include for example tank-mixes for administering an azole and, if desired, an additional active ingredient to subjects or materials. Depending upon the application technique and the nature of the subject or material where the azole, optionally combined with an additional active ingredient, is applied to the diluted mixture may be any liquid, such as, for example, aqueous- or non-aqueous mixtures, e.g. aqueous or non-aqueous dilutions, aqueous- or non-aqueous waxes and the like liquids.

The subject formulations have also the advantage that the activity of the azoles incorporated therein is positively influenced. As a consequence thereof analogous antimicrobial activities may be obtained with reduced concentrations of the azole in the mixture applied to the subject or material.

Additionally, compared with the art-known formulations the subject formulations effect also a reduced phytotoxicity of the mixtures ultimately applied to, resulting in a very useful application-mixture with a desirable safety margin.

The hereinabove-mentioned properties, combined with a substantial lack of irritation render the subject formulations particularly attractive, not only for their desirable safety margin for the subjects or materials applied to but also for the applicator.

The subject formulations may be prepared by mixing the components together at a temperature comprised between 10° C. and 100° C., preferably between 15° C. and 60° C.

The following examples are intended to illustrate and not to limit the scope of the present invention. Unless otherwise stated herein all parts therein are by weight.

Pluriol PE ®, as used in the experimental part, is a Trade Mark for a cobloc polymer consisting of polyethylene oxide- and polypropylene oxide blocks wherein the molar mass of the polypropylene oxide block is 3250 g per mole and 50% of the cobloc-polymer consists of polyethylene oxide blocks.

EXAMPLES

EXAMPLE 1

Preparation of emulsifiable concentrates formulation 1:
50% w/v imazalil;
14.5% w/v Pluriol PE ®;
7.15% w/v dodecylbenzenesulfonic acid; and
1,2-propanediol ad volume.
Preparation:
50 Parts of imazalil were mixed with 20 parts of 1,2-propanediol at 50° C. Subsequently 14.5 parts of Pluriol PE ® and 7.15 parts of dodecylbenzenesulfonic acid were added and the mixture was stirred at 20° C. until the mixture was homogeneous. Finally, the mixture was diluted to 100 ml.
formulation 2:
10% w/v imazalil;
1% w/v cypermethrin;
5% w/v Pluriol PE ®; and
1,2-propanediol ad 100 ml.
Preparation:
10 Parts of imazalil were mixed with 50 parts of 1,2-propanediol. Subsequently 1 part of cypermethrin and 5 parts of Pluriol PE ® were added and the mixture was stirred at 20° C. until the mixture was homogeneous. Finally, the mixture was diluted to 100 ml.

EXAMPLE 2

Antifungal activity

Young gherkin plants, about 10 days old, were sprayed with a mixture containing 10, 1 or 0.1 ppm of imazalil while controls were kept untreated. After drying of the plants artificial infection with spores of *Erysiphe cichoracearum* was carried out by slightly rubbing the plants with a heavily infected leaf. At the 15th day after artificial infection the degree of fungal attack was evaluated by counting the number of spots per plant.

The results given in Table 1 are the percentages of fungal attack in comparison with the untreated plants. Dilution A was prepared by diluting a xylene-based emulsifiable concentrate containing 20% of imazalil with water. Dilution B was prepared by diluting formulation 1 (described hereinabove) with water.

TABLE 1

| | percentage of fungal attack | | |
| | concentration in ppm | | |
| | 10 | 1 | 0.1 |
|---|---|---|---|
| dilution A | 0 | 20 | 50 |
| dilution B | 0 | 0 | 1 |

EXAMPLE 3

Phytotoxicity-tests

Pears (Doyennè du Comice and Conference) were immersed into an imazalil containing mixture during two minutes. After pears were leaked out during one minute they were stored on a glass petridish and stored during 5 days at 5° C. As the apples and pears were not dried before storage a moistened ring is formed between the glass petridish and the contact-surface of the pear. Fytotoxicity was measured by determining the percent of the contact-surface which shows any form of decay or discoloration.

The results given in Table 2 are the percentages of the contact-surface which shows any form of decay or discoloration at different concentrations of imazalil in the immerse-mixture.

Apples were immersed into an imazalil containing mixture during two minutes. After the apples were leaked out during one minute they were placed five together in a glass recipient of five liter and stored during 5 days at 2° C. As the apples were not dried before storage a moistened ring was formed at the contact-surfaces of the apples and the contact-surfaces formed between the apples and the glass recipient. Fytotoxicity was measured by determining the percent of the contact-surface which shows any form of decay or discoloration.

The results given in Table 3 are the percentages of the contact-surface which shows any form of decay or discoloration at different concentrations of imazalil in the immerse-mixture.

The imazalil-containing mixtures under investigation were:

dilution C, prepared by diluting formulation 1 (described hereinabove) with water;

dilution D, prepared by diluting a water-soluble powder containing 75% of imazalil sulfate with water; and dilution E, prepared by diluting a xylene-based emulsifiable concentrate containing 20% of imazalil with water.

TABLE 2

| | Phytotoxicity data on pears | |
|---|---|---|
| | Percent of decay or discoloration of the contact-surface | |
| | Doyenne du Comice | Conference |
| dilution C | | |
| 1000 ppm | 2 | 0 |
| 1500 ppm | 2 | 0 |
| 2000 ppm | 2 | 0 |
| dilution E | | |
| 250 ppm | 2 | 0 |
| 500 ppm | 5 | 1 |
| 1000 ppm | 6 | 2 |

TABLE 3

| | Phytotoxicity data on apples |
|---|---|
| | Percent of decay or discoloration of the contact-surface |
| | Golden delicious |
| dilution C | |
| 1000 ppm | 0 |
| 2000 ppm | 0.5 |
| dilution D | |
| 1000 ppm | 2 |

EXAMPLE 4

Physical compatibility

Dilutions containing 500 ppm of imazalil and 500 ppm of a mix-pesticide are prepared by diluting the initial mix-pesticide containing formulations with standard hard water (342 ppm) at 30° C., adding a calculated amount of formulation 1 and, finally, diluting with standard hard water up to the desired concentration of imazalil and mix-pesticide containing formulations with standard hard water (342 ppm) at 30° C. Blanco formulations containing only the mix-pesticide were also prepared following the same procedure. The samples were inverted up to a homogeneous mixture was obtained (number of inversion-cycles: see Table 4, column 1 for blanco and column 2 for the combination) and, subsequently, up to twenty inversion-cycles. After an immobile storage of the samples at 30° C. the samples were inverted until the formed sedimentation or creaming had completely disappeared (number of inversion-cycles: see Table 4, column 3 for blanco and column 4 for the combination).

TABLE 4

| | number of inversion-cycles | | | |
|---|---|---|---|---|
| mix-pesticide containing formulation | column 1 blanco | column 2 combination | column 3 blanco | column 4 combination |
| Vinclozolin 50% WP* | 2 | 2 | 1 | 1 |
| Thiophanate 70% WP | 1 | 2 | 1 | 2 |
| 3-(3,5-dichlorophenyl)-1-isopropylcarbamoxyl-hydantoin 50% WP | 1 | 2 | 1 | 2 |
| Carbendazin 50% WP | 2 | 2 | 2 | 2 |
| Triadimefon 25% WP | 3 | 3 | 2 | 3 |
| Carbendazin 50% FL* | 3 | 3 | 6 | 7 |
| Thiabendazol 45% FL | 3 | 8 | 2 | x |

*WP is an abbreviation for wettable powder
*FL is an abbreviation for flowable

What we claim is:

1. A method for combating fungus on a living subject or non-living organic material which comprises the steps of:

A. diluting an emulsifiable concentrate comprising:
   (i) from 1% to 60% w/v of a polyoxyethylene-polyoxypropylene block copolymer;
   (ii) from 1% to 98% w/v of an alkanediol; and
   (iii) from 1% to 60% w/v of an azole of the formula:

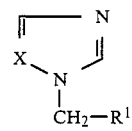

or an acid addition salt thereof, wherein X is —CH═, and wherein $R^1$ is a group of the formula:

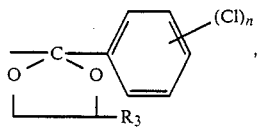

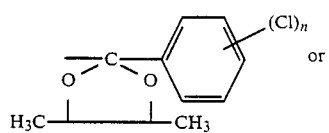

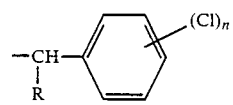

wherein n is 1 or 2, $R_3$ is hydrogen or $C_{1-3}$alkyl, and R is $C_{1-4}$alkyl or $C_{3-4}$alkenyloxy; and B. applying the diluted concentrate from Step A to said living subject or non-living organic material.

2. The method of claim 1 wherein said dilution is with an aqueous liquid.

3. The method of claim 1 wherein said living subject is a plant.

4. The method of claim 1 wherein said non-living organic material is wood, coatings, harvested fruits, foodstuffs, or medicine.

5. The method of claim 3 wherein said non-living organic material is harvested fruit, foodstuffs, or vegetables.

6. The method of claim 1 wherein the emulsifiable concentrate further comprises a biocidal compound.

7. The method of claim 1 wherein the alkanediol is 1,2-propanediol.

8. The method of claim 1 wherein R¹ is a group of the formula:

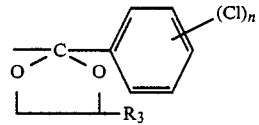

wherein n is 1 or 2, and wherein $R_3$ is hydrogen or $C_{1-3}$alkyl.

9. The method of claim 1 wherein said block copolymer contains from 30% to 60% of oxyethylene units and has a molar mass of oxypropylene units of 950 to 5000 grams per mole.

10. The method of claim 1 wherein said block copolymer contains 50% of oxyethylene units and has a molar mass of oxypropylene units of 3250 grams per mole.

11. The method of claim 1 wherein the azole is 1-[2-(2,4-dichlorophenyl)-2-(2-propenyloxy)ethyl]-1H-imidazole.

* * * * *